United States Patent [19]

Saito et al.

[11] Patent Number: 4,828,395
[45] Date of Patent: May 9, 1989

[54] CONTINUOUS FLOW TYPE HOMOGENIZER

[75] Inventors: Tatsuhiko Saito, Machida; Hikaru Takabatake, Tokyo; Hiroaki Mori, Tokyo; Masahiro Ida, Tokyo; Takeshi Orii, Yachiyo, all of Japan

[73] Assignee: Yamato Scientific Company, Limited, Tokyo, Japan

[21] Appl. No.: 809,094

[22] Filed: Dec. 13, 1985

[30] Foreign Application Priority Data

Feb. 21, 1985 [JP] Japan .................. 60-022545
Feb. 21, 1985 [JP] Japan .................. 60-022546

[51] Int. Cl.⁴ .................. B01F 13/04; B01F 15/06; B02C 19/00
[52] U.S. Cl. .................. 366/143; 366/149; 366/286; 366/331; 366/349; 366/601; 366/279; 241/2; 241/246; 241/258; 241/259; 388/847; 388/907; 388/915; 388/903
[58] Field of Search .............. 366/143, 149, 286, 331, 366/349, 601, 279, 285, 209, 1; 241/2, 246, 169.1, 169.2, 101.7, 65, 66, 258, 259; 215/13 R; 141/97; 318/384; 16/DIG. 39, DIG. 40; 192/110 S; 285/902

[56] References Cited

U.S. PATENT DOCUMENTS

| D. 229,278 | 11/1973 | Westover ............. 215/12 R |
| 1,888,503 | 11/1932 | Hoppe ................. 141/97 |
| 2,127,615 | 8/1938 | Peters et al. .......... 141/97 |
| 2,733,396 | 1/1956 | Luther ................. 366/601 |
| 2,829,931 | 4/1958 | DePree et al. ........ 366/331 |
| 2,884,230 | 4/1959 | Pyle et al. ............ 366/106 |
| 2,894,732 | 7/1959 | Taber et al. .......... 366/143 |
| 3,752,447 | 8/1973 | Chen .................. 366/149 |
| 3,920,227 | 11/1975 | Davis, Jr. ............ 366/601 |
| 3,937,447 | 2/1976 | Alwed et al. ......... 366/601 |
| 3,985,379 | 10/1976 | Normark .............. 285/902 |
| 4,207,006 | 6/1980 | Wilson ................ 366/184 |
| 4,252,446 | 2/1981 | Bauer ................. 366/279 |
| 4,264,215 | 4/1981 | Nunlist et al. ....... 366/279 |
| 4,307,846 | 12/1981 | Spelsberg ............. 241/2 |
| 4,390,825 | 6/1983 | Ginn ................... 318/384 |
| 4,531,840 | 7/1985 | Clark ................. 366/601 |
| 4,673,297 | 6/1987 | Siczer et al. ........ 366/208 |
| 4,685,179 | 8/1987 | Sheehan et al. ..... 28/271 |

FOREIGN PATENT DOCUMENTS

| 694118 | 7/1940 | Fed. Rep. of Germany ...... 241/246 |
| 958250 | 7/1957 | Fed. Rep. of Germany ...... 366/108 |
| 1433197 | 2/1966 | France ................ 318/384 |
| 0046786 | 3/1985 | Japan ................. 318/384 |
| 745940 | 7/1980 | U.S.S.R. ............. 241/2 |

Primary Examiner—Philip R. Coe
Assistant Examiner—Joseph S. Machuga
Attorney, Agent, or Firm—David A. Tucker; Robert B. Russell

[57] ABSTRACT

There is provided a continuous flow type homogenizer. The homogenizer comprises, a tubular container having at upper end thereof an inlet for introducing tissue to be homogenized and at lower end thereof an outlet for discharging the homogenized tissue, a pestle disposed freely rotatable in the tubular container with a clearance defined between the inner surface of the tubular container and the peripheral surface of the pestle, a rotation shaft driving means connected to a rotation shaft of the pestle, a speed setting means for setting the rotation speed of the pestle, and a speed controlling means for controlling the speed of the rotation shaft with a predetermined speed gradient with respect to a speed value set by the speed setting means.

15 Claims, 15 Drawing Sheets

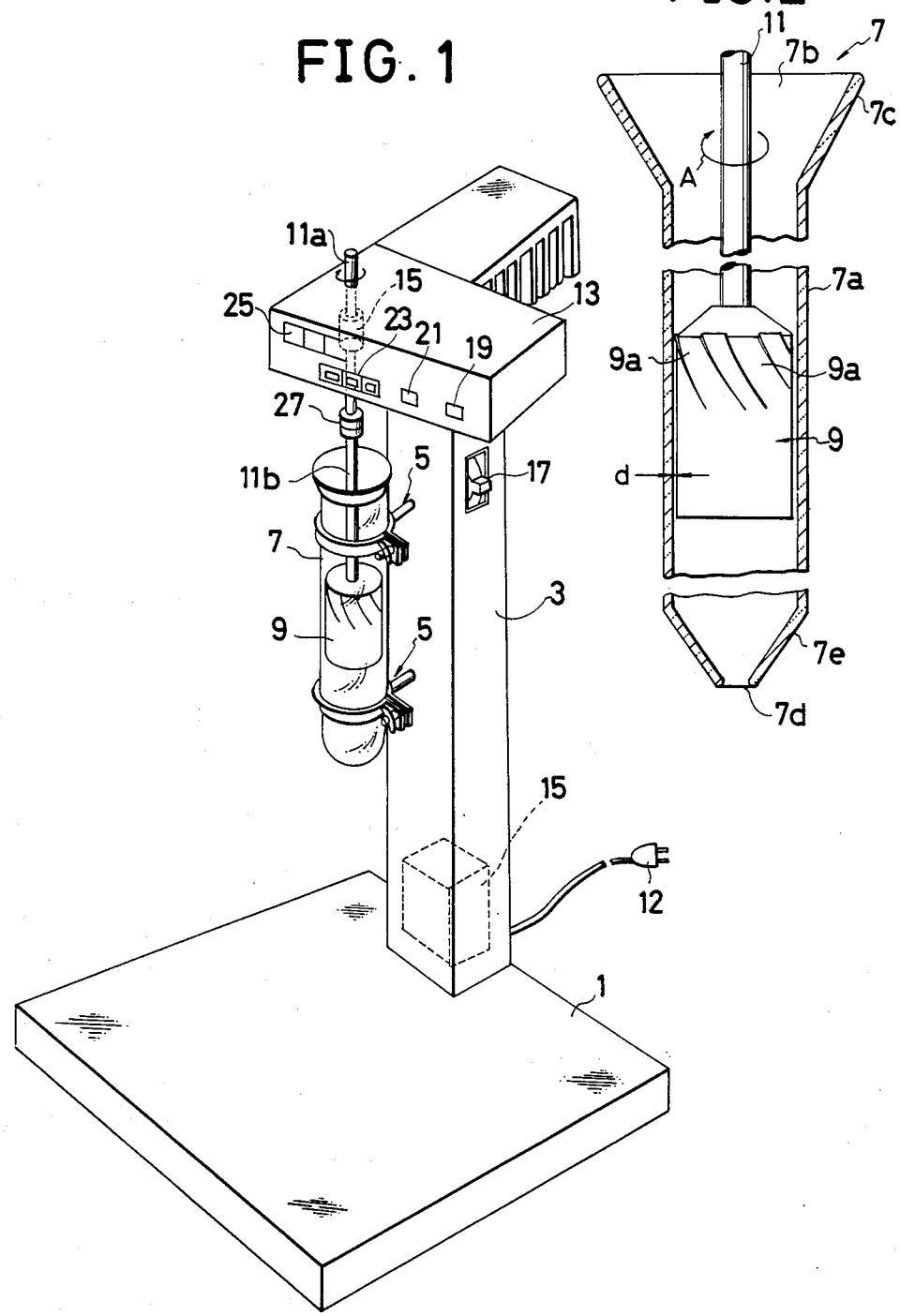

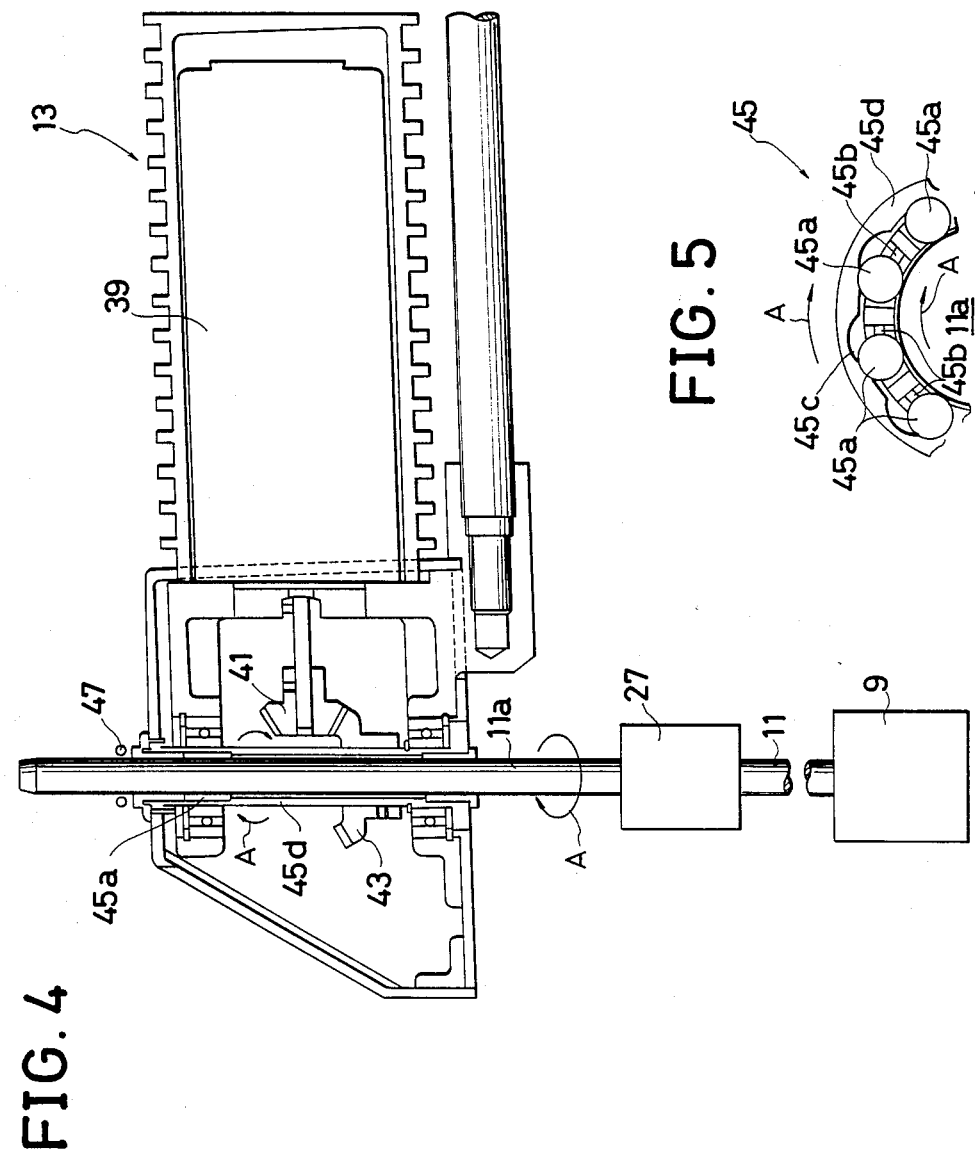

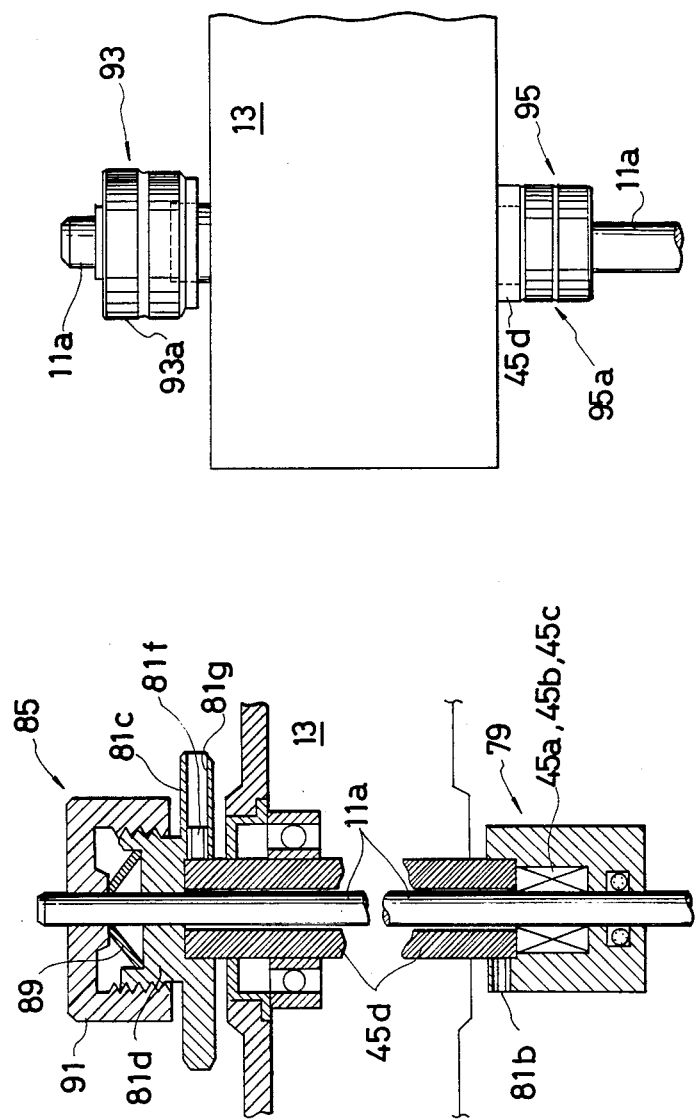

FIG. 18
FIG. 19
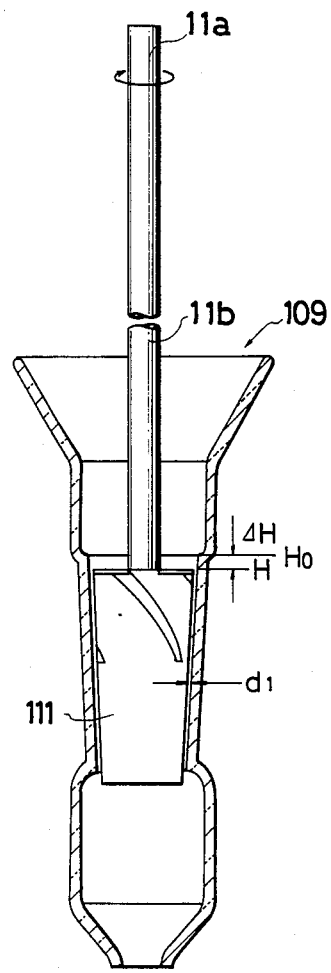
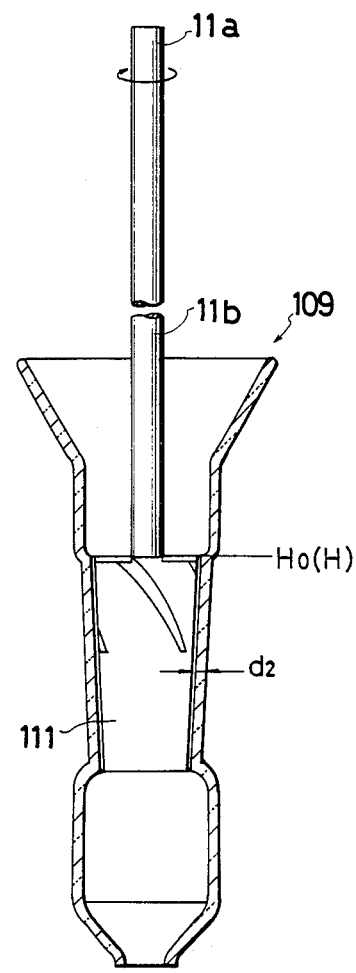

CONTINUOUS FLOW TYPE HOMOGENIZER

BACKGROUND OF THE INVENTION

1. Field of the Invention

The present invention relates to a continuous flow type homogenizer which is adapted for disrupting the cell membrane of a cell to isolate subcellular organelles, etc., included in the cell.

2. Description of the Prior Art

There is a necessity in biological, medical, and other research fields to isolate enzymes and subcellular organelles such as Golgi apparatus and mitochondria included in cells. For the isolation, the cells shall be disrupted by some disrupting means. There are several prior art means for disrupting cell membranes (the means hereinafter called the "homogenizer"), in which one utilizes ultrasonic waves, another applying nitrogen gas, etc., with high pressure and removing the pressure abruptly to disrupt the cell membranes, or the other applying pressure by hydraulic machine on cells in liquid to pass the cells through small holes to disrupt the cell membranes. There is a further prior art method which is called the potter type in which a pestle is rotated in a tubular container (hereinafter called the "cylinder") by an exclusive rotary driving unit while the cylinder is manually reciprocated up and down to disrupt the cell membranes. The pestle may be rotated in the cylinder by utilizing an existing rotary machine.

Generally, such prior art homogenizers are not efficient in disrupting cells and inconvenient in handling. For instance, a cylinder of the potter type homogenizer which is widely used shall manually be moved up and down. That reduces the efficiency of device. In other devices which use ultrasonic waves or high pressure nitrogen gas, their sizes become large, and that pushes their costs up.

In the case which uses a stirrer or an existing rotary machine to rotate a pestle, it is difficult to control the rotational speed of pestle according to the service conditions of the homogenizer, such as the nature of tissue to be homogenized. Further, the characteristic of rotational speed change of existing rotary machine, etc., is not suitable for the homogenizer. It is preferable for the homogenizer to change its speed continuously and gently with a constant velocity gradient when starting and stopping the homogenizer or during the change of its speed.

If the homogenizer is not properly rotated, or if a clearance between the pestle and cylinder is not set properly, the homogenizing operation will not properly be carried out, and undesirable friction heat may be caused to deteriorate the homogenized tissue.

Supposing tissue to be homogenized are A and B, the temperature of tissue A before the homogenization $T_A°$ C., the temperature of tissue B before the homogenization $T_B°$ C., diameter of cylinder $D_S$ mm, the material of cylinder is glass, the diameter of pestle D mm, the material of pestle is fluororesin, the linear expansion coefficient of glass at reference temperature of 20° C. "$L_G$" ($3 \times 10^{-6}$ to $20 \times 10^{-6}/°$ C.), and the linear expansion coefficient of fluororesin "$L_F$" (about $10 \times 10^{-5}/°$ C.). The change $\Delta d$ of clearance "d" is approximately given by the following equation:

$$\Delta d = D_S \cdot L_G(T_A-20) - D_p \cdot L_F(T_B-20)$$
$$\div -D_p \cdot L_F(T_B-20)$$

Namely, the $\Delta d$ varies according to the linear expansion of pestle. The value of $\Delta d$ at, for instance, 30° C. with the pestle diameter of 20 mm, reaches 0.03 mm. In other words, if there is a temperature difference of 30° C. between the tissue A and B to be homogenized, there is caused a difference of 0.03 mm in the clearance "d". Since the homogenizing operation shall be performed with the clearance being kept at 0.15 to 0.20 mm as mentioned in the above, the change of clearance in the value of 0.03 mm may effect largely on the homogenizing operation.

Other factors which will degrade the quality of homogenized tissue are the operator's erroneous observation of the operation due to the lowered transparency of container, and impurities entering from the upper opening of container.

Among potter type homogenizers described in the above, there is a kind which is covered (coated) with the polyvinyl chloride (PVC). The cover (coating) is provided to protect an operator from injuring his hands with the broken pieces of cylinder, if the cylinder is broken during the operation.

However, the cover according to prior art is formed only by coating the cylinder with thin plastics so that broken pieces may happen to break through the coating film. Further, it is difficult to observe the homogenizing condition if the transparency of the coating film is deteriorated. The transparency of the coating film is deteriorated not only when external surface thereof is damaged, but also when water enters between the cylinder and the coating film while the cylinder is being washed, or when water and air enter through pinholes that may be on the coating film. If the coating film is thickened to improve its strength, it is unavoidable that the transparency of coating film is deteriorated preventing the observation of homogenizing condition when the external surface of plastic coating film is damaged or when water enters between the cylinder and the coating film while the cylinder being washed.

SUMMARY OF THE INVENTION

An object of the present invention is to provide an improved continuous flow type homogenizer.

Another object of the present invention is to provide a continuous flow type homogenizer which has a simple constitution and is produced with low cost.

A further object of the present invention is to provide a continuous flow type homogenizer in which the rotational speed of a pestle can properly be controlled.

A further object of the present invention is to provide a continuous flow type homogenizer which realizes, the high disruption efficiency.

A further object of the present invention is to provide a continuous flow type homogenizer which is convenient in its handling.

A further object of the present invention is to provide a continuous flow type homogenizer in which a cylinder can be set and removed without removing entirely a pestle.

A further object of the present invention is to provide a continuous flow type homogenizer in which the position of a pestle with respect to a container is freely adjustable.

A further object of the present invention is to provide a continuous flow type homogenizer in which a clearance between the inner wall of a container and the peripheral wall a pestle can properly be maintained.

A further object of the present invention is to provide a continuous flow type homogenizer which can produce products with excellent reliability.

A further object of the present invention is to provide a continuous flow type homogenizer in which homogenized products are protected against external contamination.

A further object of the present invention is to provide a continuous flow type homogenizer in which homogenized products are protected against high temperature.

A further object of the present invention is to provide a continuous flow type homogenizer in which the transparency of a container can easily be maintained so that the homogenizing process may be carried under best conditions with appropriate observation being made.

The other object of the present invention is to provide a continuous flow type homogenizer in which an operator is protected from being injured due to the breakage of a container.

BRIEF DESCRIPTION OF THE DRAWINGS

These and other objects, features and advantages of the present invention will become apparent from the following description of preferred embodiments taken in conjunction with the accompanying drawings in which:

FIG. 1 is a perspective view showing a continuous flow type homogenizer according to an embodiment of the present invention;

FIG. 2 is an enlarged vertical cross-sectional view showing the cylinder portion shown in FIG. 1;

FIG. 4 is a cross-sectional view showing a rotation shaft driving unit;

FIG. 5 is a cross-sectional plan view showing the constitution of a one-way clutch;

FIG. 10 is a cross-sectional view showing a further embodiment of the height adjuster and one-way clutch;

FIG. 11 is a side view showing a still further embodiment of the height adjuster and one-way clutch;

FIGS. 18 and 19 are side views in which the cylinder and pestle shown in FIGS. 14 and 15 are engaged together, said views explaining that a clearance "d" ($d_1$, $d_2$) changes according to the positional relation between the cylinder and pestle;

DETAILED DESCRIPTION OF THE EMBODIMENTS

Figure 3A:
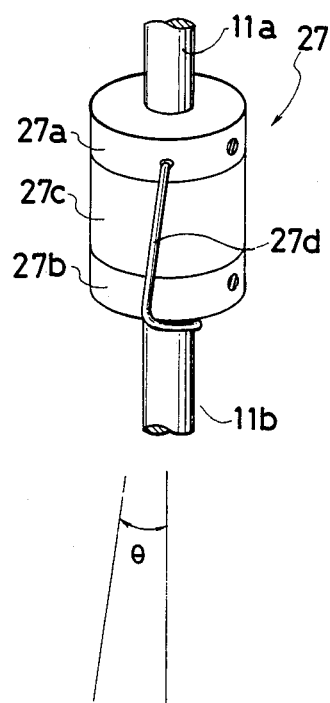
FIG. 3(A) is an enlarged perspective view showing a coupling.

As shown in FIG. 1, a continuous flow type homogenizer comprises a post 3 arranged upright on a base 1, a tubular container (hereinafter called the "cylinder") 7 supported along the post 3 with bands 5 and a pestle 9 driven in rotation in the cylinder 7, and a rotation shaft driving unit 13 for driving in rotation a rotation shaft 11a fitted to the pestle 9.

At the lower part of post 3, there is provided a plug 12 to be inserted into a socket for a commercial power source. A voltage converter 15 is accommodated inside the lower part of post 3. At the upper part of post 3, there is provided a main switch 17 for supplying the power from the voltage converter 15 to the rotation shaft driving unit 13.

The rotation shaft driving unit 13 is provided therein with a one-way clutch 15 which will be described with reference to FIG. 4. The front cover of driving unit 13 is provided with a start switch 19, a stop switch 21, a digital switch 23 for setting speed, and a speed indicator 25. The rotation shaft 11a is connected to the pestle 9 through a rotation shaft 11b, which is directly connected to the pestle 9, and a coupling 27.

As shown in FIG. 2, the cylinder 7 comprises cylindrical portion 7a, an inlet portion 7c of an inverse conical shape for introducing tissue to be homogenized, said inlet portion 7c being formed at the upper part of cylindrical portion 7a and having at its upper end an inlet 7b for introducing tissue to be homogenized, and a homogenized tissue discharging portion 7e formed at the lower part of cylindrical portion 7a, said discharging portion 7e having a discharging outlet 7d for discharging homogenized tissue. The cylinder 7 is made of the glass.

The pestle 9 comprises a Teflon bar material which outer diameter is slightly smaller than the inner diameter of cylindrical portion 7a. The peripheral surface of pestle 9 is provided toward its middle position with guiding grooves 9a for guiding the tissue to be homogenized. The upper end of pestle 9 is connected to the rotation shaft 11 and rotated in a direction "A" in the cylindrical portion 7a. The grooves 9a are provided in plural numbers with the fixed gradient of depth which becomes gradually shallow from the upper end toward the middle thereof. The depth of each groove 9a at upper end thereof is about 3 mm which decreases gradually to become zero at the middle of pestle. A clearance "d" between the pestle 9 and the cylinder 7 is set to be sufficient to disrupt cell membranes, that is usually 0.05 to 0.2 mm.

The reason why the guiding grooves 9a are provided for the pestle 9 is to supply quickly the tissue to be homogenized introduced in the inlet portion 7c into the clearance "d" and to carry out the shearing operation with high efficiency (Ref. U.S. Pat. No. 4,307,846).

Figure 3B:
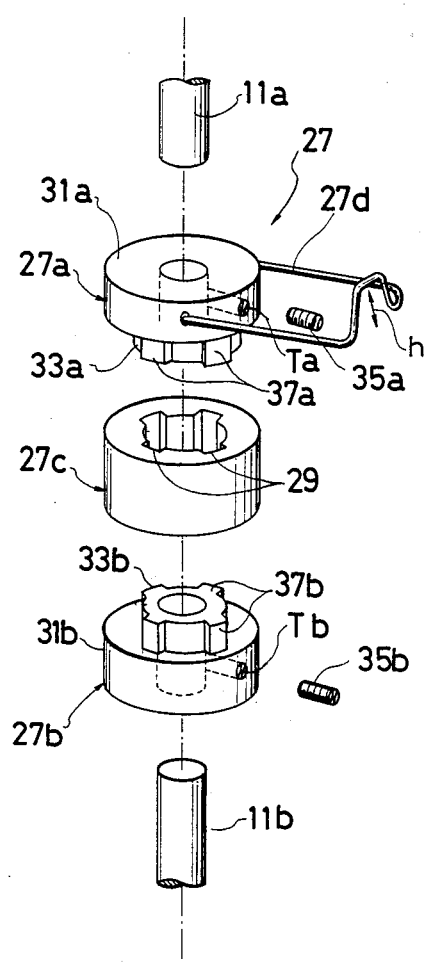
FIG. 3(B) is an exploded perspective view showing the coupling.

As shown in FIGS. 3(A) and 3(B), the coupling 27 comprises an upper joint 27a fixed to the lower end of upper rotation shaft 11a, a lower joint 27b fixed to the upper end of lower rotation shaft 11b, an intermediate joint 27c formed with a resilient member, and a clip 27d for engaging those joints together.

The upper joint 27a comprises an annular member 31a as a main body which side is provided with a tapped hole $T_a$, while lower part thereof is connected with a gear member 33a for stopping the rotation. On the both sides of annular member 31a at symmetrical positions, there are provided two small holes to which both ends of the clip 27d for assembling are hooked. The upper joint 27a and the upper rotation shaft 11a are connected to each other by inserting the lower end of rotation shaft 11a into the ring of annular member 31a and by screwing a screw 35a into the tapped hole $T_a$.

The lower joint 27b comprises an annular member 31b as a main body which side is provided with a tapped hole $T_b$, while upper part thereof is connected to a gear 33b for stopping the rotation. The lower joint 27b and the lower rotation shaft 11b are connected to each other by inserting the upper end of rotation shaft 11b into the ring of annular member 31b and by screwing a screw 35b into the tapped hole $T_b$.

The clip 27d is formed by bending a wire into a convex shape which curvature is almost the same as the outer diameter of rotation shaft 11b, and by bending further the wire orthogonally at the both sides of the convex shape. The depth "h" of the convex shape shall be sufficient that the clip 27d is kept in a state shown in FIG. 3(A) after assembling and may not be moved outwardly from said state due to the centrifugal force caused by the rotation. Namely, the depth "h" shall be such a size that the centrifugal force will act inwardly.

The coupling 27 is assembled as follows:

The upper joint 27a fixed to the upper rotation shaft 11a and the lower joint 27b fixed to the lower rotation shaft 11b are brought close to the intermediate joint 27c. The projections 37a and 37b of the rotation stopping-gear members 33a and 33b which are fitted to the upper joint 27a and lower joint 27b respectively are inserted into the upper and lower parts respectively of the grooves 29 of intermediate joint 27c. After that, the clip 27d is turned such that the clip 27d is set in a state shown in FIG. 3(A).

Due to the torsion absorbing action of intermediate joint 27c, the coupling 27 absorbs the torsion $\theta$ between the upper rotation shaft 11a and lower rotation shaft 11b to realize the smooth rotation of pestle 9. In FIG. 1, the cylinder 7 with the pestle 9 being received therein is easily attached to and removed from the post 3 so that their easy handling will be realized.

As shown in FIG. 4, the rotation shaft driving unit 13 comprises a motor 39, a bevel gear 41 connected with the rotation driving shaft of motor 39, a bevel gear 43 engaging with the bevel gear 41, a one-way clutch 45 for transmitting the driving force of bevel gear 43 to the rotation shaft 11a, and an electric circuit which will be described in detail with reference to FIG. 6.

As shown in FIG. 5, the one-way clutch 45 comprises a number of rollers 45a contacting the peripheral surface of rotation shaft 11a, said rollers 45a being spaced from one another with fixed intervals and disposed on a predetermined circumference, springs 45b for pressing the respective rollers 45a in a direction opposite to the rotating direction A, an outer driving ring 45d while the rollers 45a are pressing the springs 45b.

When the outer driving ring 45d is driven in rotation by the bevel gear 43 in the direction A, the one-way clutch 45 causes the rollers 45a to be engaged between the outer driving ring 45d and the rotation shaft 11a so that the rotation shaft 11a may be driven in rotation in the direction A. On the other hand, when the outer driving ring 45d is rotated in a direction opposite to the direction A, the rollers 45a are guided into the slant faces 45c and floated so that the rotation shaft 11a may be kept stopped. The one-way clutch 45 is attached such that the reverse rotation of rotation shaft 11a is prohibited, and the up and down position of rotation shaft 11a can be adjusted.

Above the one-way clutch 45, the rotation shaft 11a is provided with an O-ring 47 for adjusting the height of rotation shaft 11a. The inner diameter of the O-ring shall be slightly smaller than the outer diameter of rotation shaft 11a. The O-ring 47 fixes the height of rotation shaft 11a. For this purpose, an instantaneous hose fitting, a special device which will be described with reference to another embodiment, etc., may also be adopted in place of the O-ring 47.

Figure 6A:
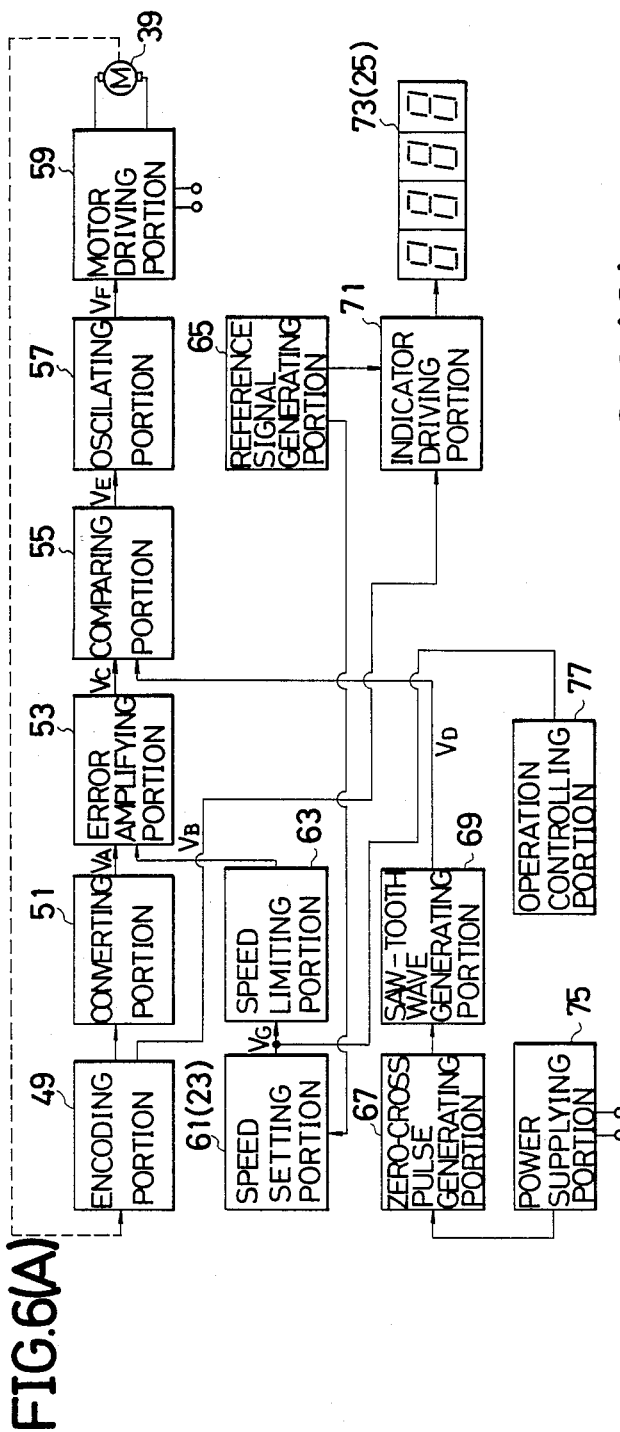
FIG. 6(A) is a block diagram showing an electric circuit.

As shown in FIG. 6, the electric circuit of rotation shaft driving unit 13 comprises an encoding portion 49, an F/V converting portion 51, an error amplifying portion 53, a comparing portion 55, an oscillating portion 57, a motor driving portion 59, a speed setting portion 61 (corresponding to the digital switch 23 shown in FIG. 1), a speed limiting portion 63, a reference signal generating portion 65, a zero-cross pulse generating portion 67, a sawtooth wave generating portion 69, an indicator driving portion 71, an indicating portion 73 (corresponding to the indicator 25 shown in FIG. 1), a power supplying portion 75, and an operation controlling portion 77 (corresponding to the start switch 19 and the stop switch 21 shown in FIG. 1).

The encoding portion 49 is to obtain a pulse signal proportional to the revolution of motor 39. The pulse signal is supplied to the error amplifying portion 53 and the indicator driving portion 71.

The F/V converting portion 51 converts the pulse signal from the encoding portion 49 into DC voltage $V_A$ to generate high voltage when the number of pulses is large, and low voltage when it is small. The generated voltage is supplied to the error amplifying portion 53.

The error amplifying portion 53 finds the error ($V_B - V_A$) of the speed command voltage $V_B$ from the speed controlling portion 63 which will be described later and the voltage $V_A$ from the F/V converting portion 51, moves the central voltage (for instance, 5 volts) according to the error, and decides the output voltage $V_C$ to supply the output voltage to the comparing portion. If the output pulse from the encoding portion 49 coincides with the command speed, the output voltage becomes to be equal to the central voltage (5 volts in this embodiment), and, if the output pulse is lower than the command speed, the output voltage becomes lower than 5 volts.

The comparing portion 55 compares the voltage $V_C$ with the sawtooth voltage $V_D$ from the sawtooth wave generating portion 69 which will be described later, and outputs a voltage signal $V_E$ to the oscillating portion 57, said voltage signal $V_E$ being ON (high level) when $V_D \geq V_C$, and OFF (low level) when $V_D < V_C$. Therefore, if the output of encoding portion 49 is lower than the command speed, the lower part of sawtooth voltage $V_D$ is cut, and the comparing portion 55 extends (makes high duty) the duration of ON level signal.

The oscillating portion 57 outputs an oscillation signal VF while the output signal $V_E$ from comparing portion 55 being high level.

The motor driving portion 59 receives AC power from the power supplying portion 75, which is connected to a commercial power source, and provides the power to the motor 45 through a thyristor. The thyristor becomes conductive according to the high level signal from the oscillating portion 57. Accordingly, if the output signal from the encoding portion 49 is lower than the command speed, the motor 39 is driven with high duty to increase the speed.

The speed setting portion 61 is set by a digital switch, for instance in the revolutions per minute (r.p.m.). The speed setting portion 61 incorporates a counter, and receives clock pulses from the reference signal generating portion 65 to count for a predetermined time the set value of the revolutions per minute. The count for the predetermined time, i.e., the duty proportional to the set value thus obtained is passed through a filter to generate voltage $V_G$ proportional to the set value, said voltage $V_G$ being outputted to the speed limiting portion 63.

Figure 6C:
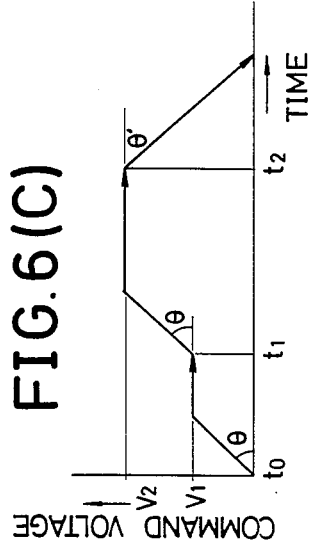
FIG. 6(C) is a speed characteristic curve of a motor.
Figure 6B:
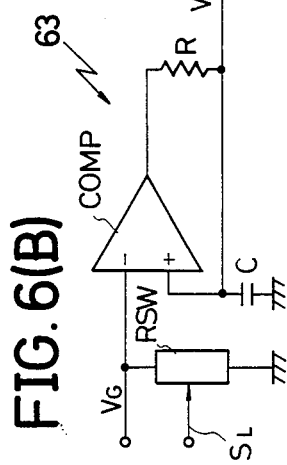
FIG. 6(B) is a circuit diagram showing a speed controlling portion.

As shown in FIG. 6(B), the speed limiting portion 63 has a comparator COMP the terminals (+) and (−) of which are connected to a capacitor C which is grounded and the output $V_G$ from the speed setting portion 61 respectively. The output of comparator COMP is outputted through a resistor R. The output terminal and the input terminal (+) are short-circuited. An output line from the speed setting portion 61 is connected to a switching circuit SL from the operation controlling portion 77. If a high level signal is supplied, a logic switch RSW will be activated to set the voltage $V_G$ of speed setting portion 61 zero and lower the output. Although the logic switch RSW has been located between the speed setting portion 61 and the speed limiting portion 63, it can be incorporated inside the speed setting portion 61.

As shown in FIG. 6(C), supposing the speed command of command voltage $V_1$ is given at a time $t_0$. The speed limiting portion 63 does not output the voltage $V_1$ as it is, but increases the same with a fixed gradient ($\theta$). After the command. voltage $V_1$ is reached, the voltage $V_1$ is outputted. If the command voltage is changed to $V_2$ at a time $t_1$, the output voltage is gradually increased up to the changed value in the same manner as before. If the command voltage is set to zero at a time $t_2$, the output voltage becomes zero with fixed gradient ($\theta'$). When the logic switch RSW is operated, the same thing as the case when the command voltage is set to zero will happen. For an emergency stop, the main switch 17 is turned OFF, or the ($\theta'$) is made larger.

The reference signal generating portion 65 supplies clock pulses to the speed setting portion 61 and also to the indicator driving portion 71.

The zero-cross pulse generating portion 67 generates pulse signals with the zero voltage of full-wave rectification obtained from the same power source as that of the motor 39.

The sawtooth wave generating portion 69 generates a sawtooth wave for each pulse received from the zero-cross pulse generating portion 67 and outputs the generated wave to the comparing portion 55.

The indicator driving portion 71 incorporates a counter, and receives the clock pulses from the reference signal generating portion 65 and the pulse signals from the encoding portion 61 to count the pulses from the encoding portion 61. The result of counting is outputted to the speed indicating portion 73 through a driver.

The speed indicating portion 73 comprises LEDs to cause light emission from seven segments properly to indicate the number of revolutions of motor. The power supplying portion 75 is connected to a commercial power supply which is adequately changed or rectified and supplied to the motor driving portion 59, the zero-cross pulse generating portion 67, and other portions.

The operation controlling portion 79 treats the start switch 19 or the stop switch 21 shown in FIG. 1, and supplies the result to the logic switch RSW shown in FIG. 6(B). The controlling portion 79 incorporates a logic circuit. When the start switch 19 is turned ON, the logic switch RSW is opened, and, when the stop switch is turned ON, the logic switch RSW is closed to set the output voltage of speed setting portion 61 zero. If the both switches are operated, the stop switch is given priority.

According to the above-mentioned constitution of electric circuit, the motor 39 performs a smooth operation so that no abnormal force may be applied on the pestle 9.

The homogenizing operation will be described with reference to FIG. 1.

The homogenizer is assembled as shown in FIG. 1 and adjusted so that the pestle 9 comes to a required height in the cylinder 7. The height of pestle 9 can be adjusted by moving the rotation shaft 11a up and down freely within the one-way clutch 45. Since the coupling 27 (Ref. FIG. 3) is interposed between the rotation shafts 11a and 11b, the rotation shaft 11b is not required to be adjusted precisely so that the assembling will be made easily.

The switch 17 is turned ON to set the digital switch 23 to a required speed value, and then the start switch 19 is turned ON. The rotation, shaft 11a increases its rotating speed as shown in FIG. 6C to the required value, said speed value being indicated on the speed indicator 25.

Tissue to be homogenized (cells in liquid) is introduced from the inlet 7c, and sent along the peripheral surface of pestle 9 shown in FIG. 2 into the guiding grooves 9a and clearance d. Cell membranes are disrupted between the outer surface of pestle 9 and the inner surface of cylinder 7, and the homogenized tissue is continuously discharged from the outlet 7d. During the operation, the position of pestle 9 can easily be changed after stopping temporarily the motor. Due to the provision of the one-way clutch 45 as well as the coupling 27 between the rotation shafts 11a and 11b, the homogenizer is handled conveniently. After completing the homogenization, the motor is stopped, and the bands 5 are removed to take the cylinder 7 out of the post 3.

The continuous flow type homogenizer shown in FIGS. 1 to 6 realizes the excellent rotational speed characteristic of pestle 9 due to a good speed characteristic given to the rotation shaft 11, high efficiency in cell disruption due to the grooves 9a cut on the pestle 9, easy handling, and simple operation.

Four other embodiments of the one-way clutch and height adjuster will be described.

Figure 7:
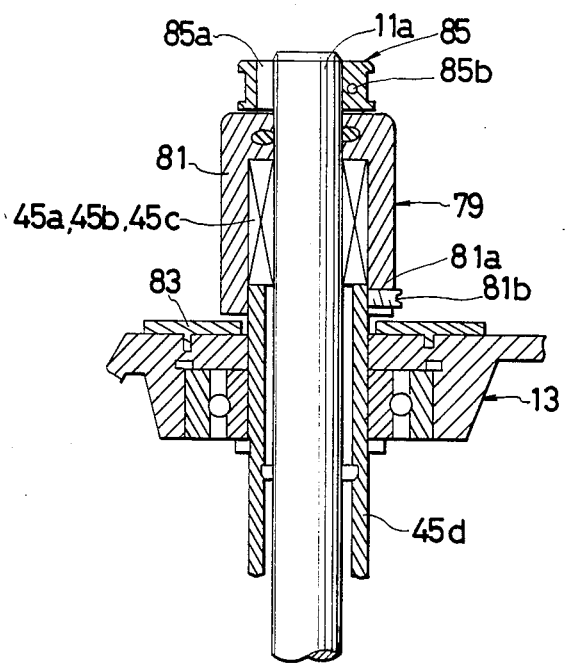
FIG. 7 is a cross-sectional view showing a height adjuster and another embodiment of the one-way clutch.

As shown in FIG. 7, a one-way clutch 79 is located at the upper end of the casing of rotation shaft driving unit 13 shown in FIG. 4. The casing 81 includes one-way clutch mechanisms such as the rollers 45a, springs 45b, and slant faces 45c which are the same as those shown in FIG. 5. At one part of the lower end periphery of casing 81, there is formed a screw hole 81a to which a set screw 81b is screwed. The end of screw 81b abuts against a machined section (not shown) located at the upper end of a pipe shaft 45d (corresponding to the outer driving ring 45d shown in FIG. 5) to connect the housing 81 with the pipe shaft 45d. The housing 81 is revolved with the pipe shaft 45d. The numeral 83 represents a seat to support smoothly the housing 81.

In this embodiment, a height adjuster which differs from the one shown in FIG. 4 (O-ring) is provided for adjusting the height of rotation shaft 11a. The height adjuster, 85 is formed with an annular member having an expanding slot 85a extending along a diameter thereof completely through the wall on one side and partially through the wall on the opposite side thereof. The bottom of adjuster 85 is located on the upper surface of casing 81. An expanding slot screw 85b connects the open ends of slot 85a where it passes completely through the wall of adjuster 85. The base of the slot 85a acts like a spring biased hinge such that when screw 85b is tightened the open end of slot 85a is drawn together releasably grasping the rotation shaft 11a.

The height adjuster 85 can be moved up and down along the rotation shaft 11a with the screw 85b being unfastened, said screw 85b being fastened after the rotation shaft 11a comes to a required height to fix the height of rotation shaft 11a, i.e., the height of pestle 9 to the required height. The one-way clutch 79 can be removed from the rotation shaft driving unit 13 if the set screw 81b is unfastened.

The height adjuster 85 described in the embodiment can adjust the height of rotation shaft 11a to a required position so that the height of pestle 9 may be freely and correctly adjusted. Further, the one-way clutch 79 can be removed from the main body of rotation shaft driving unit 13 by unfastening the set screw 81b to replace the clutch with new one if it is damaged due to abrasion, corrosion, etc.

Figure 8:
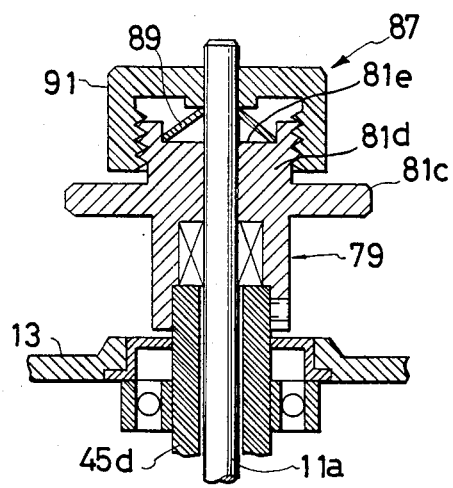
FIG. 8 is a cross-sectional view showing still another embodiment of the height adjuster and one-way clutch.
Figure 9:
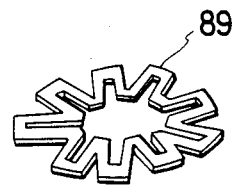
FIG. 9 is a perspective view showing a spring member incorporated in the height adjuster shown in FIG. 8.

A height adjuster 87 shown in FIGS. 8 and 9 is solidly made with the one-way clutch 79 shown in FIG. 7. The height adjuster 87 comprises a flange 81c and a threaded bar 81d provided at the top of the casing of one-way clutch 79, a recessed portion 81e provided at the top of threaded bar 81d, an angle spring member 89 received in the recessed portion 81e, the outer diameter of said angle spring member 89 being smaller than the inner diameter of said recessed portion, the inner diameter of said angle spring member 89 being larger than the outer diameter of the rotation shaft 11a if no external pressure is applied on the angle spring member 89, and a cap 91 screwed onto the threaded portion of threaded bar 81d, the rotation shaft 11a passing through the cap 91, said cap 91 pressing the spring member 89 to contract the inner diameter of spring member 89.

In this embodiment, the cap 91 is turned with respect to the flange 81c to contract the spring member 89 which inner diameter fixes the rotation shaft 11a to the cap 91. As a result, not like the case shown in FIG. 7, the height of rotation shaft 11a can easily be adjusted without using tools such as a screwdriver.

A one-way clutch and a height adjuster shown in FIG. 10 are the improvements of those shown in FIG. 8. A height adjuster 85 is constituted on the upper side of the casing of rotation shaft driving unit 13, while a one-way clutch 79 is separately constituted on the lower side of the casing of rotation shaft driving unit 13. In this embodiment, a compact design is realized by screwing a set screw 81f, which is for fixing the rotation shaft 11a to the pipe shaft 45d, into a long hole 81g provided on the flange 81c.

Similar to the clutch shown in FIG. 8, the one-way clutch 79 shown in this embodiment can easily be fitted to and removed from the casing of rotation shaft driving unit 13.

A height adjuster 93 and a one-way clutch 95 shown in FIG. 11 are further improvements of those shown in FIG. 10. The flange 81c shown in FIG. 10 has been removed from the height adjuster 93. A cap 93a which corresponds to the cap 91 is knurled. The casing 95a of one-way clutch 95 which is the same as that shown in FIG. 10 is also knurled.

According to the height adjuster 93 and one-way clutch 95, the casing 95a of one-way clutch 95 is grasped by a hand to turn the cap 93a of height adjuster 93 by another hand. After loosening the cap 93a, the rotation shaft 11a is moved upwardly or downwardly to adjust a height thereof to a required level. Then, the cap 93a is fastened again. Accordingly, the height of rotation shaft 11a can easily be adjusted without using tools.

Figure 12:
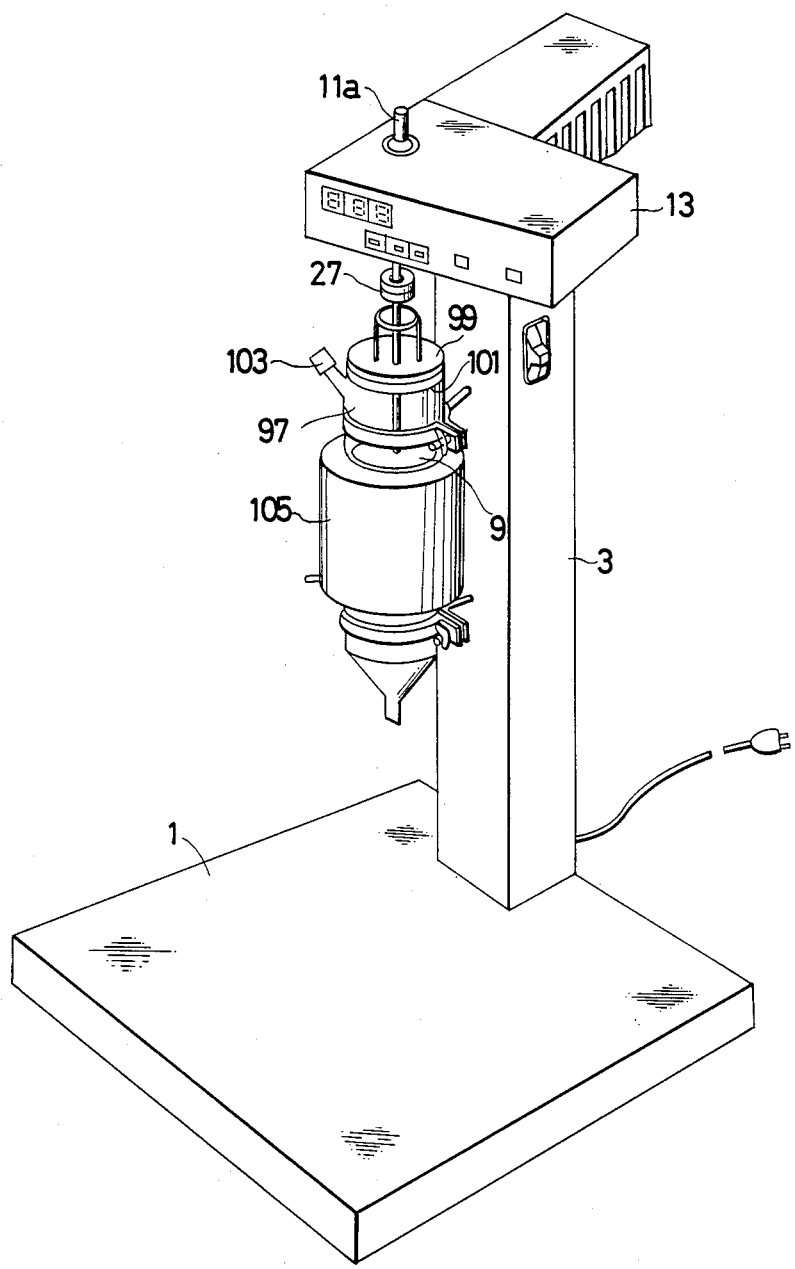
FIG. 12 is a perspective view showing another embodiment of the continuous flow type homogenizer.
Figure 13:
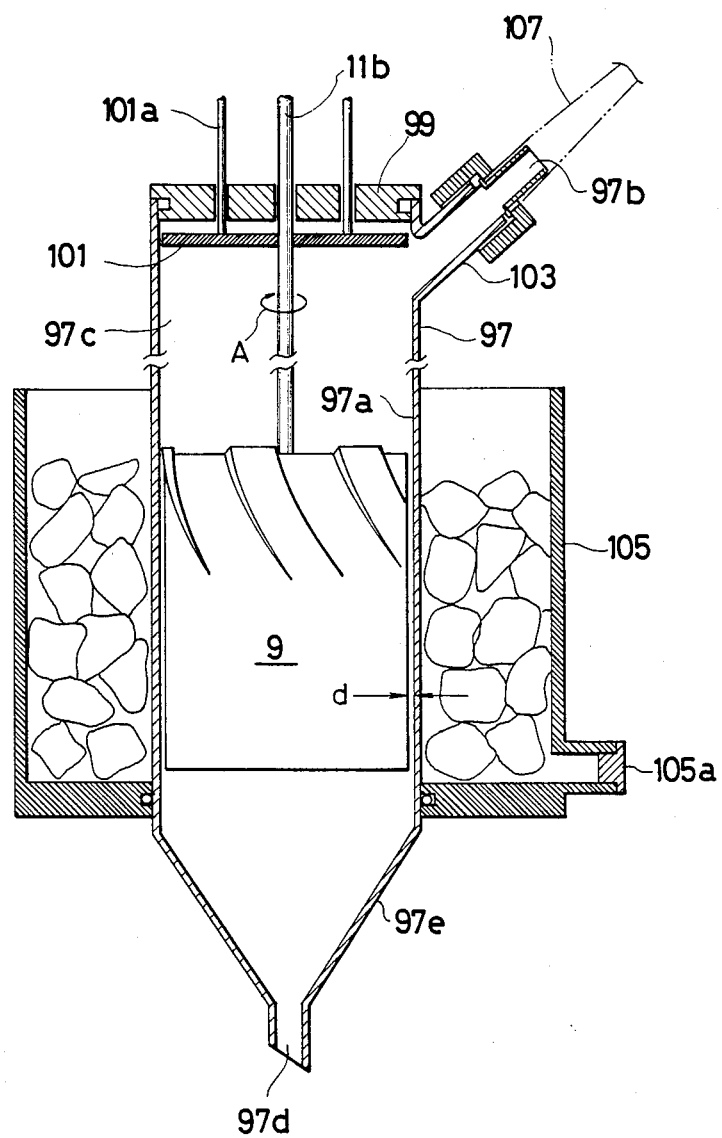
FIG. 13 is an enlarged cross-sectional side view showing a cylinder portion of the continuous flow type homogenizer shown in FIG. 12.

FIGS. 12 and 13 show another embodiment in which an improved cylinder portion is adopted.

As shown in FIGS. 12 and 13, the upper end of a cylinder 97 of this embodiment is covered with a cap 99. Just below the cap, a disk like pressure plate 101 is arranged movable up and down. A nipple is fitted to the upper part of cylinder 97 near the cap 99. A cooling apparatus 105 is fitted around the cylinder 97.

The cap 99 seals the top of cylinder 97 to prevent contaminant such as dust from entering the cylinder 97 during the homogenization as well as preventing the sample in the cylinder from splashing outside. This is important to protect environment from contamination, since isotopes, etc., are sometimes used as the sample.

At the upper end of pressure plate 101, a handle 101a is fitted to move the pressure plate 101 up and down in the cylinder 97. The pressure plate 101 applies pressure for the tissue to be homogenized introduced into the tissue inlet portion 97c.

One end of nipple 103 forms a tissue inlet mouth 97b connected to a hose 107, said nipple guiding the tissue to be homogenized supplied from the hose 107 to the upper part of cylinder 97.

The cooling apparatus 105 comprises a jacket surrounding the homogenizing portion 97a of cylinder 97. Coolant such as ice is filled in the jacket to cool the periphery of cylinder 97 down to a predetermined temperature. The numeral 105a represents a plug.

According to the continuous flow type homogenizer shown in this embodiment, the cap 99 protects the products (homogenized tissue) from contamination to improve the quality of products. Due to the provision of nipple 103, tissue to be homogenized will continuously be poured into the cylinder from the hose 107 so that the operability may be improved. Further, by moving the pressure plate 101 up and down, the tissue to be homogenized in the tissue inlet portion 97c will be stirred and applied with pressure so that the stabilized quality of products may be realized with a highly efficient homogenizing operation.

Due to the cooling apparatus, the periphery of cylinder 7 is cooled to absorb heat generated in the clearance "d" during the homogenizing operation so that the quality of homogenized products will be improved, and the sticking in the clearance "d" will be prevented.

FIGS. 14 to 19 show another embodiment in connection with a cylinder shape.

Figure 14:
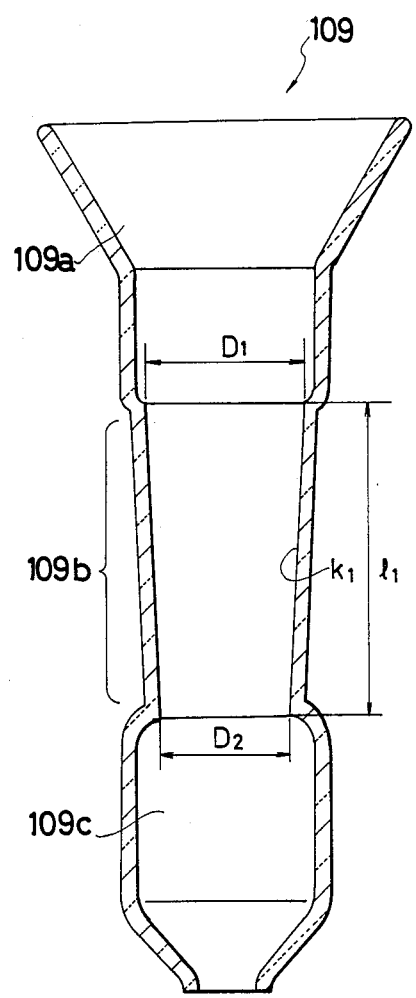
FIG. 14 is a cross-sectional side view showing another embodiment of the cylinder.

As shown in FIG. 14, a cylinder 109 comprises an inlet portion 109a for introducing tissue to be homogenized, a homogenizing portion 109b, and a discharging portion 109c for discharging homogenized tissue. Through the inlet portion 109a, tissue to be homogenized is poured, and the homogenized tissue discharging portion 109c discharges the homogenized tissue sent from the homogenizing portion 109b into a container (not shown) through a lower end mouth. The cylinder shown in this embodiment is made of the glass.

The homogenizing portion 109b is formed with its length $l_1$, upper end diameter $D_1$, and lower end diameter $D_2$, and with a tapered face of the gradient $k_1$ (1/20).

Figure 15:
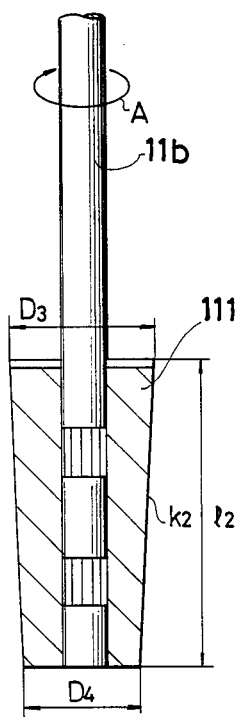
FIG. 15 is a cross-sectional side view showing a pestle to be engaged with the cylinder shown in FIG. 14.
Figure 16:
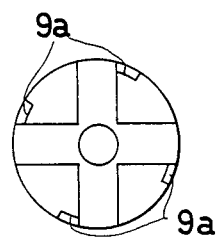
FIG. 16 is a plan view showing the pestle shown in FIG. 15.
Figure 17:
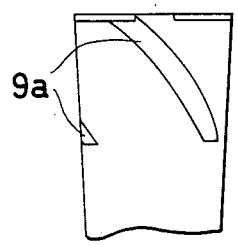
FIG. 17 is a side view showing the upper portion of the pestle.

As shown in FIGS. 15 to 17, a pestle 111 is connected to the rotation shaft 11b. The side face of pestle 111 is provided with four shallow grooves 9a (Ref. FIG. 2) formed from the upper end of pestle 111 toward middle thereof to draw the tissue to be homogenized according to the rotation of pestle 111. The rotation shaft 11a is knurled to prevent slipping to be caused between the rotation shaft 11a and pestle 111.

The pestle 111 is formed in a tapered shape of the length $l_2$ and the gradient $k_2$ with the diameter of upper end $D_3$ and the diameter of lower end $D_4$. In this embodiment, $l_1=l_2$ and $k_1=k_2$ are established. It is set to cause the clearance of 0.20 mm between the homogenizing portion 109b and the pestle 111, when the height of the upper end of pestle 111 is aligned with the position of the upper end of the homogenizing portion 109b of cylinder 109. The pestle shown in this embodiment is made of the fluororesin.

FIGS. 18 and 19 show the adjusting method of the height of pestle.

As shown in FIG. 19, if the upper end height H of pestle 111 is aligned with the upper end height $H_0$ of homogenizing portion 109b, the clearance $d_2$ becomes 0.20 mm. As shown in FIG. 18, if the upper end height H of pestle 111 is descended to a position which is lower by $\Delta h$ than the upper end height $H_0$ of homogenizing portion 109b, there is realized a clearance d1 which is smaller by $\Delta H.k_1$. Since the gradient $k_1$ is 1/20 in this embodiment, if $\Delta H=1$ mm, the clearance $d_1$ becomes 0.15 mm.

Accordingly, upon using the cylinder 109 and pestle 111 shown in FIGS. 14 to 19, it is realized to obtain a required clearance "d" between the pestle and cylinder by adjusting the height of pestle 111 with respect to the homogenizing portion 109b.

The adjustment of clearance can properly be performed to absorb the change of clearance due to the change of temperature, or according to the kind of tissue to be homogenized or the degree of abrasion of pestle 111.

Although the taper gradient of homogenizing portion 109 and pestle 111 has been set to 1/20 in the above embodiment, the taper gradient will not be limited by said value. It is sufficient if the homogenizing portion and pestle are configured such that the clearance is changed by changing the heights of the pestle and homogenizing portion.

According to the homogenizer of this embodiment in which the homogenizing portion is formed with a tapered face having different diameters at upper and lower ends thereof, and the height of pestle which is rotated in the cylinder is freely adjustable, it is realized to set properly under several conditions the clearance between the homogenizing portion and pestle so that the operation efficiency and the products accuracy will be improved.

FIGS. 20 to 25 show a continuous flow type homogenizer of a safety improved constitution.

Figure 20:
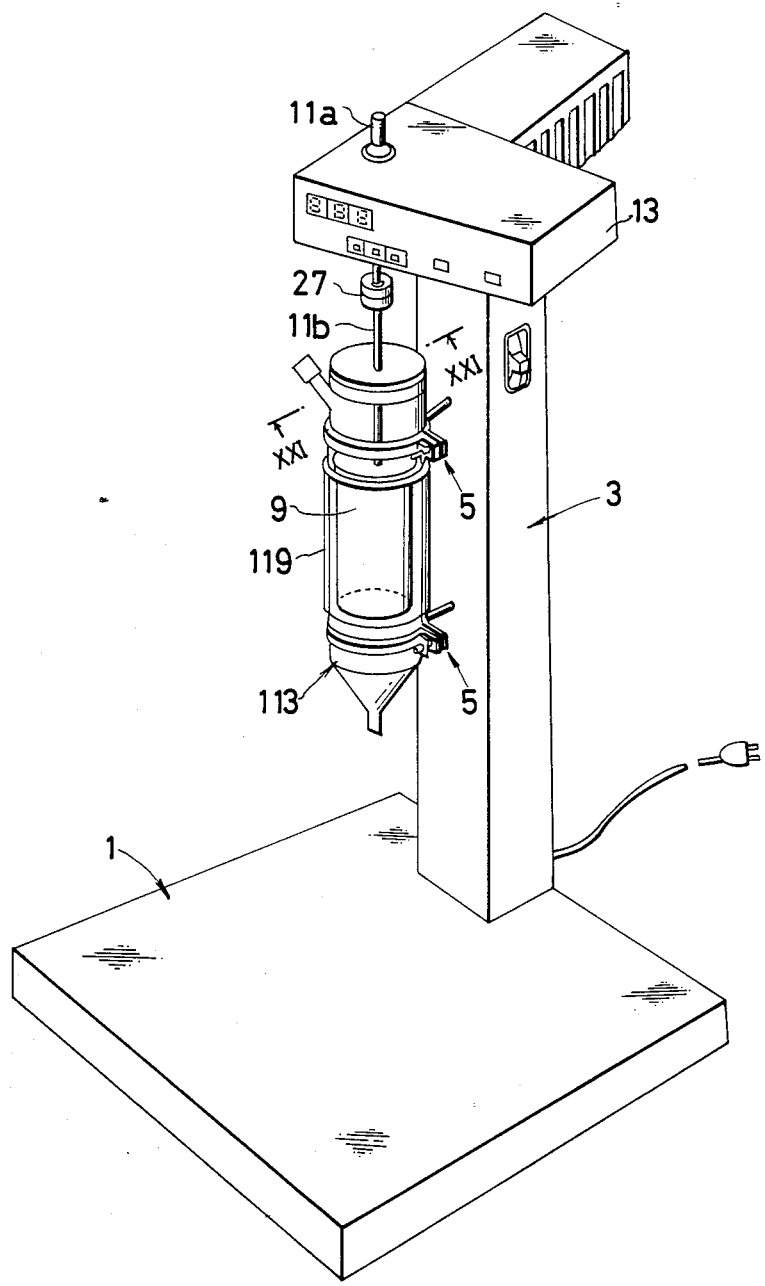
FIG. 20 is a perspective view showing a continuous flow type homogenizer which is equipped with a transparent cover arranged outside the cylinder to improve the safety.
Figure 21:
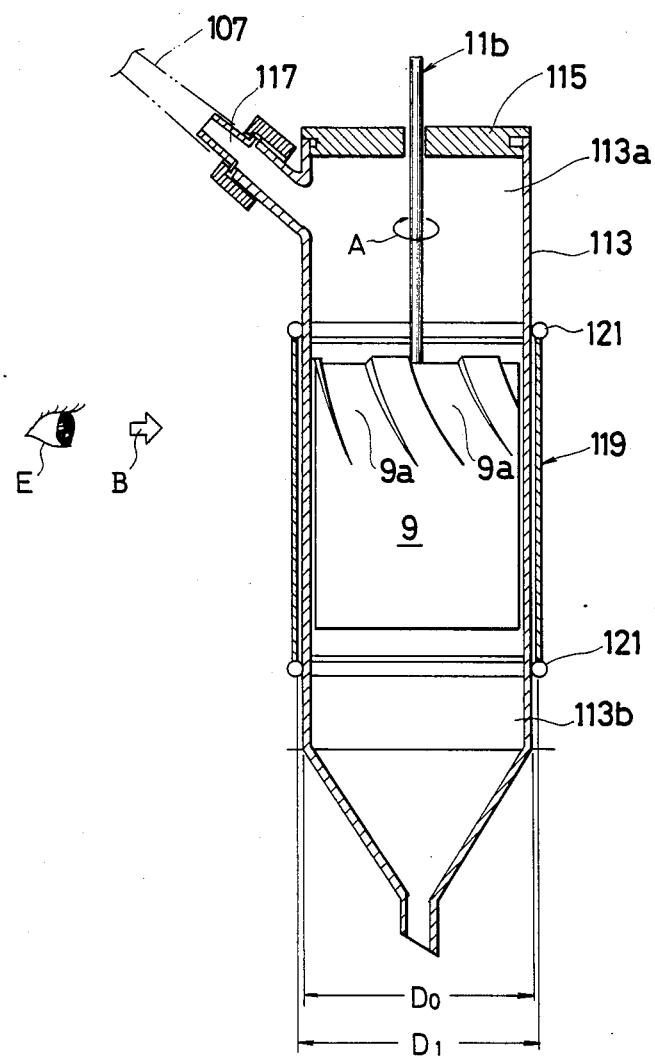
FIG. 21 is an enlarged side view showing the cylinder portion shown in FIG. 20.

According to the embodiment shown in FIGS. 20 to 21, a cylinder 113 is made of the transparent glass, upper part thereof forming an inlet portion 113a for introducing tissue to be homogenized, and lower portion thereof forming a homogenized tissue discharging portion. The inlet portion 113a for introducing tissue to be homogenized is covered with a cap 115 which is similar to the one shown in FIG. 13 and connected with a nipple 117. The nipple 117 is connected to a hose 107. The cap 115 is provided for the inlet portion 113a for introducing tissue to be homogenized to prevent, like the case shown in FIG. 13, contaminant from entering the upper opening during the homogenizing operation as well as preventing the sample in the cylinder from splashing outside.

The homogenized tissue discharging portion 113b is funneled to discharge the homogenized tissue from its end. Outside the cylinder 113, a transparent cover 119 having an inner diameter of $D_1$ which is larger than the outer diameter $D_0$ of cylinder is fitted.

The transparent cover 119 is formed in a cylindrical shape by the acrylic material and fixed outside the cylinder 113 with an O-ring 121. The thickness of transparent cover 119 is, for instance, 1 mm which will be the one sufficiently safe against the breakage of cylinder 113.

In FIG. 21, supposing the pestle 9 is rotated with high speed in the cylinder 113 to homogenize tissue introduced in the inlet portion 113a and discharge the homogenized tissue from the discharging portion 113b. The situation is supposed to be observed in a direction B with eyes E.

In this case, the homogenizing situation performed in the clearance between the pestle 9 and cylinder 113 can be observed through the cylinder 113 made of the glass and the transparent cover 119 made of the acrylic material. Even if the cylinder 113 is broken due to the expansion of pestle caused by friction heat, etc., the broken pieces will never reach the eyes E, because the thickness of transparent cover 119 is sufficiently selected. Accordingly, the operator can observe the homogenizing operation free from fear.

After finishing the homogenizing operation, the cylinder 113 is removed from support fittings (bands) 5 shown in FIG. 1, the pestle 9 taken out of the cylinder, the O-ring 121 removed, the transparent cover 119 taken out of the cylinder 113, and the cylinder 113 cleaned. The transparent cover 119 can be replaced with new one as and when required before the transparency is deteriorated to disturb the observation.

According to the homogenizer of the present embodiment in which the transparent cover 119 is adopted, the homogenizing situation can be safely observed with simple constitution so that the homogenized tissue of high quality will be obtained.

Figure 22:
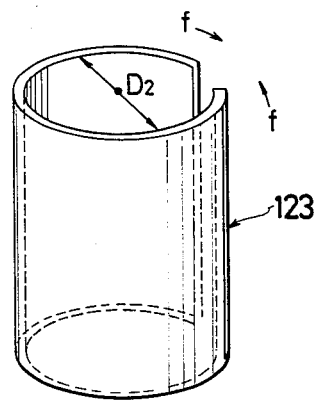
FIG. 22 is a perspective view showing another example of the transparent cover.

A transparent cover 123 shown in FIG. 22 comprises a cylindrical member having an inner diameter $D_2$ smaller than the outer diameter $D_0$ of the cylinder 113 shown in FIG. 21, said cylindrical member being cut longitudinally at one part so that it may have a C-shape cross section. The cover 123 is made of the acrylic material same as the one shown in FIG. 21, and have the same thickness as that of the one shown in FIG. 21.

The transparent cover 123 is used in place of the transparent cover 119 shown in FIG. 21. When the transparent cover 123 is assembled to the cylinder 113, it is tightly attached on the outer wall of cylinder 113 with a self elastic force "f", because the diameter $D_2$ is smaller than the diameter of cylinder 113. In this embodiment, therefore, a fitting such as the O-ring 121 shown in FIG. 2 is not required.

A continuous flow type homogenizer provided with the transparent cover 123 according to the present embodiment can also realize the safe observation of the homogenizing situation to obtain the homogenized tissue of high quality.

Figure 23:
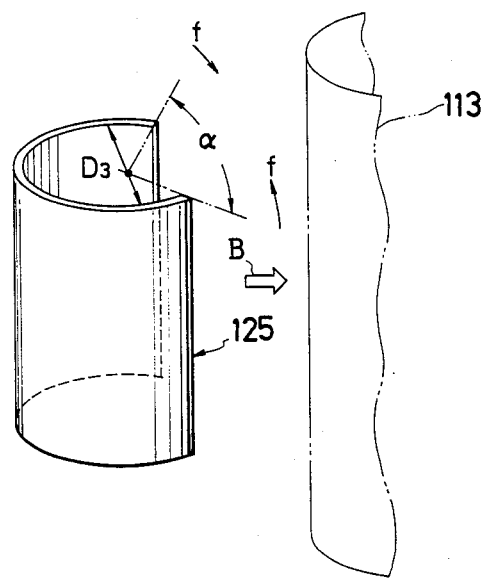
FIG. 23 is a perspective view showing still another example of the transparent cover.

A transparent cover 125 shown in FIG. 23 has a cut which is larger than that of the transparent cover 123 shown in FIG. 22. The cut angle $\alpha$ is, for instance, 150°. The inner diameter $D_3$ is, like the inner diameter $D_2$ shown in FIG. 22, smaller than the outer diameter $D_0$ of cylinder 113.

Since the cut angle a of transparent cover 125 is larger than that of the cover shown in FIG. 22, the cover 125 can be engaged with the cylinder 113 by pressing the cover in a lateral direction B as shown in the figure. After the engagement, the cover is fixed to the cylinder with friction force in the same manner as that shown in FIG. 21. Accordingly, the cylinder 113 is allowed to be firstly assembled with the support fittings 5, and the transparent cover 125 can then be fitted.

A homogenizer provided with the transparent cover 125 according to the present embodiment demonstrates the same effects realized by the examples shown in FIGS. 20, 21, and 22, and, further, an effect that the transparent cover 125 is able to be fitted to the cylinder 113 from a lateral direction so that the operability may be improved.

Figure 24:
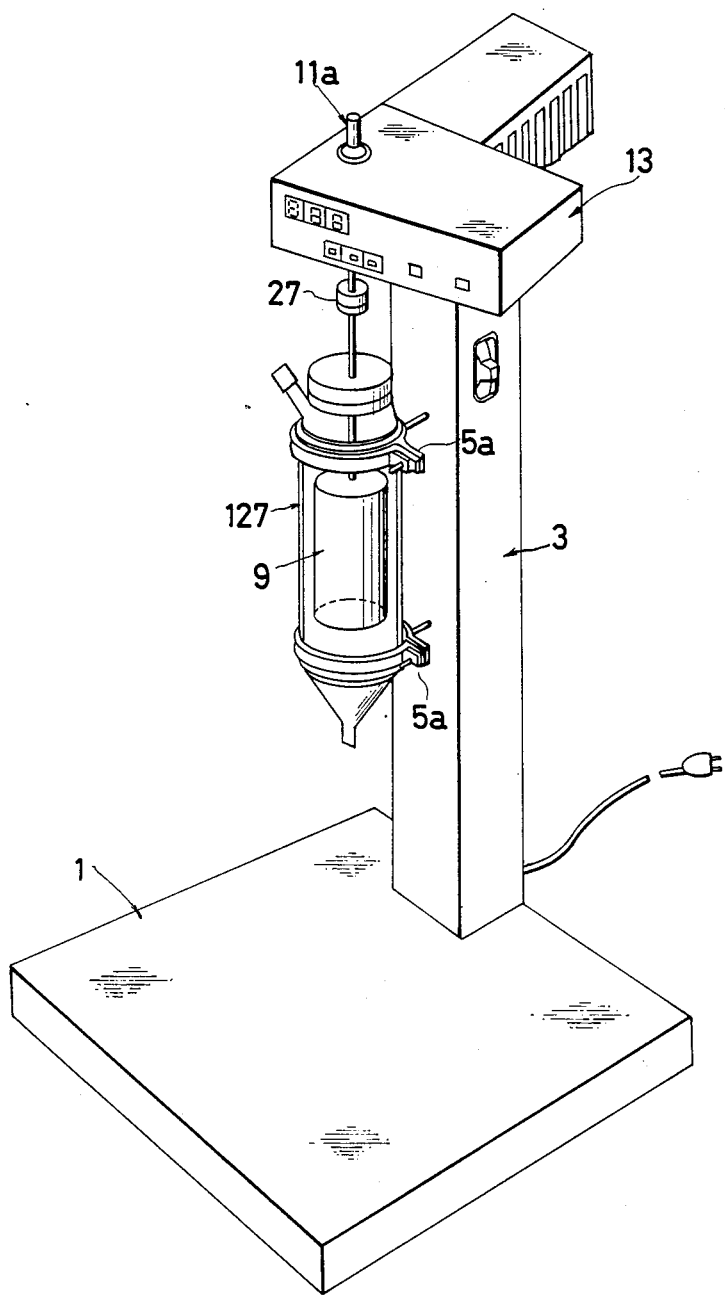
FIG. 24 is a perspective view showing another embodiment of the continuous flow type homogenizer equipped with the transparent cover arranged outside the cylinder to improve the safety.
Figure 25:
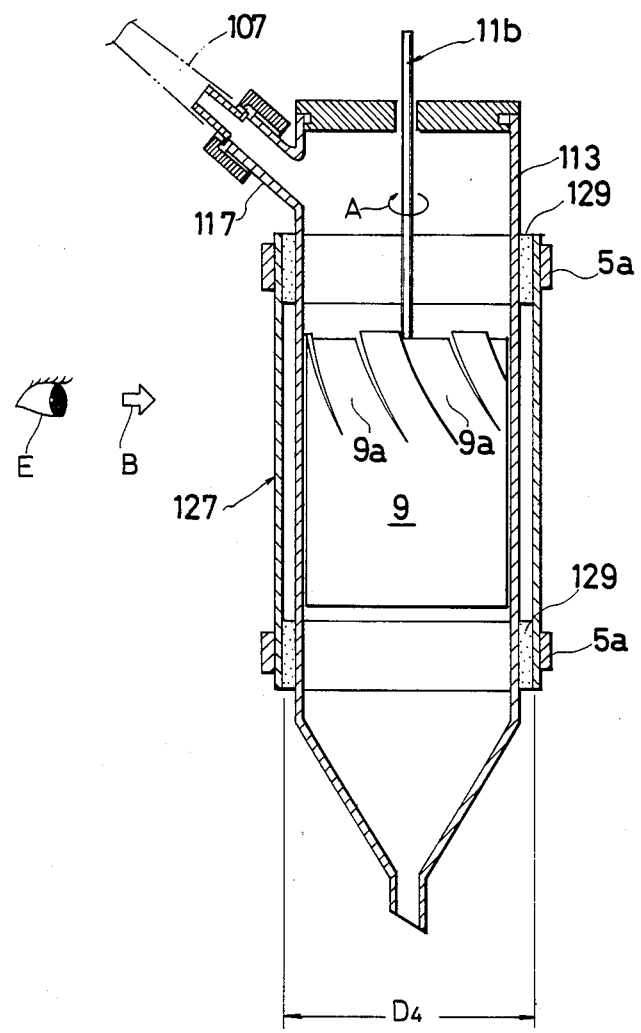
FIG. 25 is an enlarged side view showing the cylinder portion shown in FIG. 24.

A continuous flow type homogenizer shown in FIGS. 24 and 25 differs from the one shown in FIGS. 20 and 21 in that a different transparent cover 127 is provided therewith, and the size of support fittings 5a is slightly larger than that of the fittings shown in FIGS. 20 and 21.

The transparent cover 127 comprises, like the transparent cover 123 shown in FIG. 22, a cylindrical member, one part of which is longitudinally cut. The material and the thickness of the cover 127 are the same as those of the transparent cover 123 shown in FIG. 22. However, the inner diameter $D_4$ of cover 127 is larger than the outer diameter $D_0$ of cylinder 113, and the length of cover 127 is slightly longer than the distance between support fittings 5a provided vertically spaced on the post 3. As shown in FIG. 25, resilient members such as sponge members 129 are adhered inside the transparent cover 127 at locations corresponding to the locations of support fittings 5a.

The transparent cover 127 is fixed to the post 3 together with the cylinder 113 by fastening the support fittings 5a to press the sponge members 129 against the outer wall of cylinder 113.

According to the homogenizer shown in this embodiment, the homogenizing situation can be observed by eyes E in a direction B to obtain the homogenized tissue of high quality.

Although the transparent covers 119, 123, 125, and 127 are made of the acrylic material, any transparent material can be used for the transparent cover 119, and any resilient and transparent material can be used for the transparent covers 123, 125, and 127.

According to the continuous flow type homogenizer having a safety improved constitution provided with a transparent cover, the homogenizing situation can safely be observed so that the homogenizing operation may be maintained at the best condition to obtain the homogenized tissue of high quality.

What is claimed is:

1. A continuous flow-type homogenizer, comprising:
a tubular container having an inner surface and at an upper end of the container an open inlet for the continuous introduction of tissue to be homogenized and, at a lower end thereof, an outlet for discharging the homogenized tissue;
a pestle having a peripheral surface including an upper portion and a middle portion and being disposed freely rotatable in said tubular container with a clearance defined between said inner surface of said tubular container and the peripheral surface of said pestle, and said pestle further defining a plurality of grooves in the peripheral surface thereof for feeding the introduced tissue toward the outlet of said tubular container, said grooves extending from said upper portion of said peripheral surface into the middle portion thereof, each of said grooves having a gradient of depth along its length such that it becomes gradually shallower as it proceeds from said upper portion toward and into said middle portion;
a rotation shaft connected to said pestle;
a rotation shaft driving means connected to the rotation shaft connected to said pestle;
a speed setting means for setting the rotation speed of said pestle according to the kind of tissue to be homogenized; and,
a speed controlling means for controlling the acceleration/deceleration of said rotation shaft with a predetermined speed gradient with respect to a speed value set by said speed setting means during all periods of change of speed of said pestle, wherein said predetermined speed gradient is set such that the rotational speed of the pestle is gently accelerated when rotation of the pestle is started and the rotational speed is gently decelerated when the rotation is stopped and also such that the rotational speed is gently accelerated or decelerated when the rotational speed of the pestle is changed during the operation of the homogenizer so as to assure accurate and repeatable tissue homogenization conditions within said tubular container with reduced risk of homogenizer failure and/or tissue scattering from the open inlet of the container into the environment external to the container.

2. A continuous flow type homogenizer of claim 1, further comprising a one-way clutch through which a driving force is transmitted from said rotation shaft driving means to said rotation shaft.

3. A continuous flow type homogenizer of claim 1, further comprising a cap provided for the tissue introducing inlet of said tubular container.

4. A continuous flow type homogenizer of claim 1, further comprising a cooling means arranged outside said tubular container.

5. A continuous flow type homogenizer of claim 1, further comprising an adjusting means for adjusting the relative height of said pestle with respect to said tubular container.

6. A continuous flow type homogenizer of claim 5, wherein the inner surface of said tubular container is tapered, said inner surface facing to the outer surface of said pestle to form a clearance therebetween to carry out the cell disruption.

7. The continuous flow type homogenizer of claim 6 wherein the outer surface of the pestle is tapered with a gradient similar to that of the taper of the inner surface of the tubular container.

8. A continuous flow type homogenizer of claim 5, wherein said adjusting means comprises a means which moves up and down on the rotation shaft.

9. The continuous flow type homogenizer of claim 5, wherein the adjusting means comprises means for releasably gripping the rotating shaft.

10. The continuous flow type homogenizer of claim 9, wherein the gripping means comprises a spring means that clamps onto the rotation shaft when compressed.

11. A continuous flow type homogenizer of claim 1, further comprising a safety cover which is freely fitted to and removeable from said tubular container.

12. A continuous flow type homogenizer of claim 11, wherein said cover is at least partly transparent so that, the homogenizing process performed in said homogenizer may be observed through said cover.

13. The continuous flow type homogenizer of claim 11, wherein the safety cover comprises a transparent flexible material in a cylindrical shape having an inner diameter smaller than the outer diameter of the tubular container and further having a longitudinal cut so that the cover may be expanded to fit over the container.

14. The continuous flow type homogenizer of claim 1, further comprising a safety cover of transparent flexible material in a cylindrical shape having an inner diameter smaller than the outer diameter of the tubular container and further having a longitudinal cut so that the cover may be expanded to fit over the container.

15. A continuous flow type homogenizer as set forth in claim 1 wherein said rotation shaft is connected to the pestle by means of a resilient coupling.

* * * * *